(12) United States Patent
Haran-Ghera et al.

(10) Patent No.: US 6,579,525 B1
(45) Date of Patent: Jun. 17, 2003

(54) PHARMACEUTICAL COMPOSITIONS COMPRISING ERYTHROPOIETIN FOR TREATMENT OF CANCER

(75) Inventors: Nechama Haran-Ghera, Tel Aviv (IL); Moshe Mittelman, Petach-Tikva (IL); Alpha Peled, Rishon LeZion (IL)

(73) Assignees: Yeda Research and Development Co. Ltd., Rehovot (IL); Mor Research Applications Ltd., Petach Tikva (IL)

(*) Notice: Subject to any disclaimer, the term of this patent is extended or adjusted under 35 U.S.C. 154(b) by 0 days.

(21) Appl. No.: 09/647,761

(22) PCT Filed: Mar. 30, 1999

(86) PCT No.: PCT/IL99/00186

§ 371 (c)(1),
(2), (4) Date: Oct. 5, 2000

(87) PCT Pub. No.: WO99/52543

PCT Pub. Date: Oct. 21, 1999

(30) Foreign Application Priority Data

Apr. 8, 1998 (IL) .................................................. 124015

(51) Int. Cl.$^7$ ........................ A61K 39/00; A61K 38/00; A01N 61/00
(52) U.S. Cl. ............................... 424/198.1; 424/184.1; 514/1; 514/21
(58) Field of Search ............................ 514/8, 21, 814; 424/184.1, 198.1

(56) References Cited

FOREIGN PATENT DOCUMENTS

| | | |
|---|---|---|
| EP | 0 668 351 | 8/1995 |
| WO | 98/10650 | 3/1998 |

OTHER PUBLICATIONS

Gura (Science, 1997, 278:1041–1042).*
Jain (Sci. Am., 1994, 271:58–65).*
Curti (Crit. Rev. in Oncology/Hematology, 1993, 14:29–39).*
Hartwell et al (Science, 11997, 278:64–1068).*
Mittelman et al (Acta Haematol., 1997, vol. 99(4), 204–10, abstract).*
Kasper et al (Eur. J. Haematol., 1997, vol. 58(4):251–6, abstract).*
Ex parte Novitski, 26 USPQ2d 1389 (Bd. Pat.App. & Inter. 1993.*
Morere et al., "Treatment of Advanced Kidney Cancer Using Recombinant Erythropoietin," Progress in Urology, (Jun. 1997), pp. 399–402.
Rubins, J., "Metastatic Renal Cell Carcinoma: Response to Treatment with Human Recombinant Erythropoietin," Annals of Internal Medicine, vol. 122, No. 9, May 1995.

* cited by examiner

Primary Examiner—James Housel
Assistant Examiner—Gary B. Nickol
(74) Attorney, Agent, or Firm—Browdy and Neimark, P.L.L.C.

(57) ABSTRACT

Pharmaceutical compositions comprising erythropoietin are provided for treatment of cancer, particularly for treatment of multiple myeloma. Erythropoietin was found to be effective for inhibition of tumor growth, triggering of tumor regression, stimulation of the natural immunological defense against cancer and/or inhibition of cancer cell metastasis.

6 Claims, 15 Drawing Sheets

PHARMACEUTICAL COMPOSITIONS COMPRISING ERYTHROPOIETIN FOR TREATMENT OF CANCER

CROSS REFERENCE TO RELATED APPLICATION

The present application is the national stage under 35 U.S.C. 371 of PCT/IL99/00186, filed Mar. 30, 1999.

FIELD OF THE INVENTION

The present invention relates to erythropoietin and the use thereof in the treatment of cancer.

ABBREVIATIONS

BTR—blood transfusion requirements; Epo—erythropoietin; Hb—hemoglobin; MM—multiple myeloma; PS—performance status; rHuEpo—recombinant human erythropoietin.

BACKGROUND OF THE INVENTION

Human erythropoietin (Epo) is a 30.4 kD glycoprotein hormone primarily produced and secreted by the kidneys. Epo normally circulates in the bloodstream and serves as the main erythroid hormone, i.e. it is responsible for the regulation and control of red blood cell production through stimulation of the proliferation and differentiation, as well as maintaining survival, of the erythroid series (Spivak et al., 1991; Mittelman, 1993). Epo interacts with a specific receptor located on the bone marrow (BM) erythroid progenitors burst-forming unit-erythroid (BFU-E) and mainly colony-forming unit-erythroid (CFU-E).

Israel Patents IL 73785, 96581, 96582 and 100935 and corresponding U.S. Pat. Nos. 5,441,868, 5,547,933, 5,618,698 and 5,621,080 describe for the first time the DNA sequence encoding human Epo and the purified and isolated polypeptide having part or all of the primary structural conformation and the biological properties of naturally occurring Epo. An isolated Epo glycoprotein is disclosed that has the in viva biological activity of causing bone marrow cells to increase production of reticulocytes and red blood cells and is useful for treatment of blood disorders, such as anemia. International PCT publication WO 91/05867 describes Epo isoforms obtained by expression of exogenous DNA in eukaryotic host cell and said to be useful for increasing hematocrit levels in mammals by increasing production of reticulocytes and red blood cells.

European Patent Application EP 358463 discloses a method for purification of Epo intended for use in the treatment of anemia, including that found in patients on renal dialysis for kidney failure, anemia associated with cancer, aplastic anemia, anemia due to blood loss and anemia associated with chronic renal disease, and to increase red blood cell mass prior to blood donation. U.S. Pat. No. 4,745,099 describes compositions comprising Epo for treating anemia caused by malignant tumors. Japanese Patent No. 2632014 describes therapeutic agents containing human Epo as active substance for treatment of anemia caused by bone marrow dysfunction, or due to radiation exposure or administration of carcinostatic substance.

Cloning of the Epo gene (Lin et al., 1985) and introduction of recombinant human Epo (rHuEpo) into clinical practice gave hope to many patients suffering from anemia. The first to benefit from rHuEpo therapy were patients with end stage renal failure, since they lack endogenous Epo production because of the non functioning kidneys (Eschbach et al., 1989). The high success rate with these patients led to a large series of clinical trials, achieving varying results in increasing hemoglobin (Hb) and ameliorating anemia associated with AIDS (Henry et al., 1992), chronic diseases (Schreiber et al., 1996), and various malignancies such as solid tumors, myelodysplastic syndromes and multiple myeloma (Ludwig et al., 1990, 1993a and 1993b; Spivak, 1994; Mittelman et al., 1992 and 1997; Cazzola et al., 1995).

In all the above-mentioned patent documents and medical literature Epo is indicated only for the treatment of anemia. Two recent articles described treatment of renal cell carcinoma with Epo: Rubins (1995) described transient tumor regression in a single patient with renal cell cancer who had been treated with Epo for anemia, and Morere et al. (1997) reported a study of 20 patients with metastatic renal cell carcinoma who received rHuEpo: one patient achieved "complete anti-tumor response", another patient demonstrated partial response and 2 minor responses were further observed. These isolated observations with renal cell cancer patients do not indicate nor suggest a broad use of Epo in other malignancies.

SUMMARY OF THE INVENTION

It has now been surprisingly found according to the present invention that erythropoietin triggers immune responses that affect tumor regression and thus can be used in the treatment of cancer.

The present invention thus relates to pharmaceutical compositions for the treatment of cancer, excepting renal cell cancer, comprising erythropoietin and a pharmaceutically acceptable carrier. These compositions are useful for inhibition of tumor growth, triggering of tumor regression, stimulation of the natural immunological defense against cancer and/or inhibition of cancer cell metastasis.

The compositions of the invention can be used for treatment of solid tumors such as, but not being limited to, bladder, breast, cervix, colon, esophagus, larynx, liver, lung, ovary, pancreas, prostate, stomach, thyroid, uterus, vagina and vocal cord cancer, as well as of non-solid malignant neoplasms such as, but not being limited to, neoplasms of the blood-forming tissues such as leukemias, for example chronic lymphocytic leukemia (CLL), neoplasms of the reticuloendothelial and lymphatic systems such as lymphomas, and plasma cell dyscrasias such as multiple myeloma.

Any form of biologically active erythropoietin may be used according to the invention. These forms of biologically active erythropoietin include, but are not limited to, recombinant erythropoietin and analogs as described in U.S. Pat. Nos. 5,441,868, 5,547,933, 5,618,698 and 5,621,080 as well as human erythropoietin analogs with increased glycosylation and/or changes in the amino acid sequence as those described in European Patent Publication No. EP 668351 and the hyperglycosylated analogs having 1–14 sialic acid groups and changes in the amino acid sequence described in PCT Publication No. WO 91/05867. In a most preferred embodiment, the erythropoietin is recombinant human erythropoietin.

The invention relates also to the use of erythropoietin for the preparation of a medicament for the treatment of cancer, excepting renal cell cancer.

In a further aspect, the invention provides a method for treatment of cancer, excepting renal cell cancer, which comprises administering to a cancer patient an amount of erythropoietin effective for inhibition of tumor growth, triggering of tumor regression, stimulation of the natural immunological defense against cancer and/or inhibition of cancer cell metastasis in said patient.

DETAILED DESCRIPTION OF THE INVENTION

Figure 1:
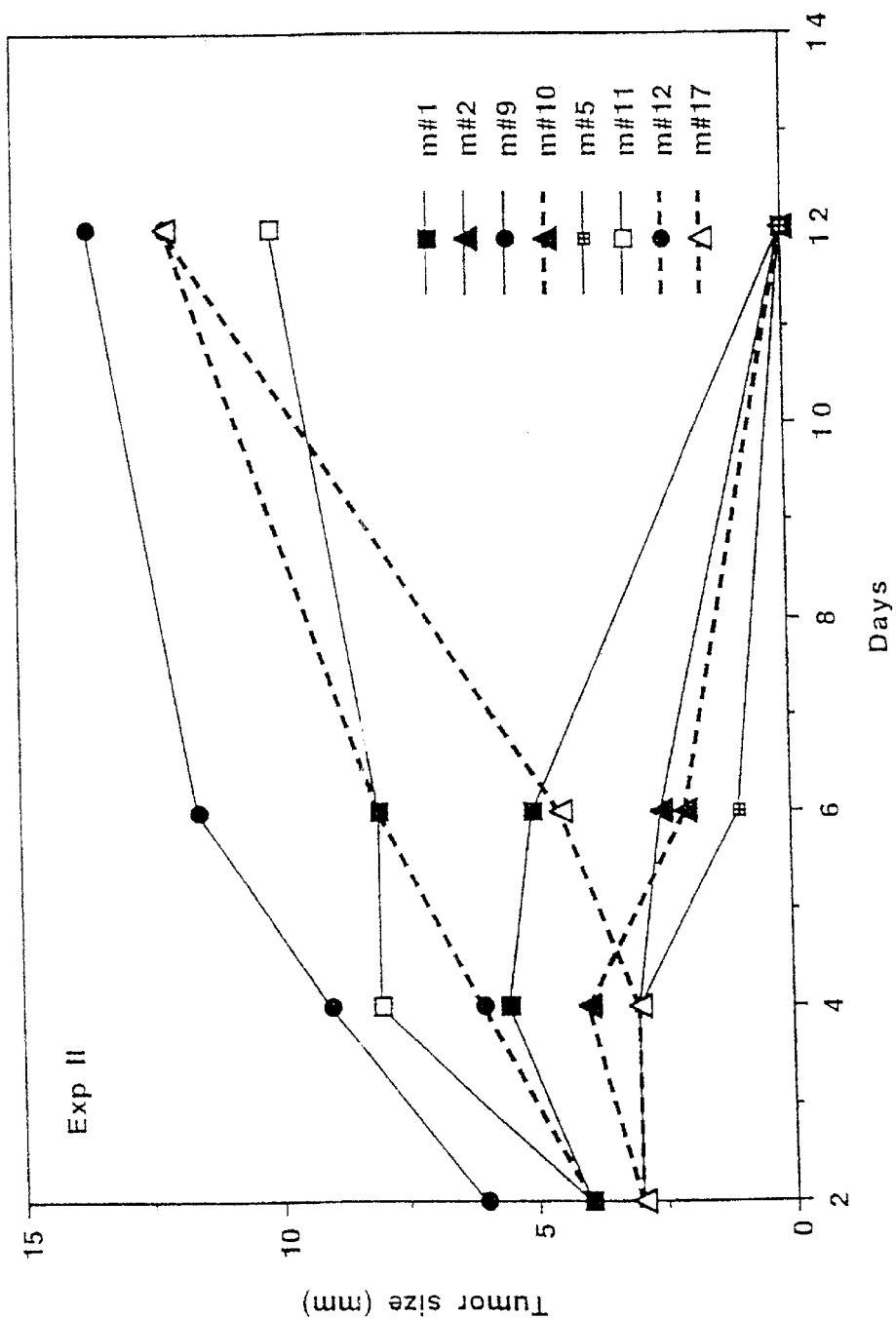
FIG. 1 shows the rate of tumor growth in progressor and regressor mice of Exp. II described in Example 2 herein. Mice # 1,2,5,9,10 were treated with rHuEpo (30 U per injection). Mice # 11,12,17—controls. Days: following rHuEpo treatment.

According to the present invention, erythropoietin, that has been used so far only for the treatment of anemia, including cancer patients suffering from anemia, was found now to affect tumor regression in mice and to improve the biological and clinical course of some multiple myeloma patients.

The first observations according to the invention were derived from multiple myeloma (MM) patients being treated for anemia, with Epo. MM is characterized by a clonal proliferation of bone marrow (BM) transformed plasma cells (PC) secreting a paraprotein which can be detected in the serum and/or urine (Kyle, 1975; Durie & Salmon, 1975; Bergsagel, 1990). The manifestations and complications of MM include anemia, recurrent infections, thrombocytopenia with bleeding episodes, pathological bony fractures, hypercalcemia, renal failure, neuropathy and amyloidosis. Most patients die of MM or its complications with a median survival ranging from 15 months (for patients who do not respond to chemotherapy) up to 48 months among responders (Bergsagel, 1990).

About 60–90% of the patients with MM suffer from anemia, which adversely affects their quality of life (Kyle, 1975; Durie and Salmon, 1975; Bergsagel, 1990). The anemia occurring in myeloma patients is associated with inadequate endogenous Epo production that can be ameliorated by exogenous Epo administration, resulting in a significant increase in their Hb level and improved quality of life (Spivak, 1994; Mittelman et al., 1997; Miller et al., 1990).

The demonstration that inadequate endogenous Epo production is among the major factors responsible for cancer-associated anemia (Miller et al., 1990), was the rationale for our phase II/III Epo-MM clinical trial described in Mittelman et al., 1997. In this trial, 17 patients with MM and anemia (Hb<11 g/dL), were treated for anemia with rHuEpo, 150 U/Kg×3/week subcutaneously. If no response was observed after 4 weeks the dose was doubled. The study was designed for 12 weeks, although a few responders continued rHuEpo for longer periods. As reported and summarized in Mittelman et al., 1997, the pretreatment endogenous serum Epo levels were relatively low in all patients studied with MM-associated anemia, rHuEpo was well tolerated in these patients, rHuEpo was highly effective in the treatment of anemia in MM, and the response to rHuEpo is characterized by an increase in Hb levels, a reduction in blood transfusion requirements (BTR) and an improvement in the WHO performance status (PS) score: out of the 17 patients, 12 (70.6%) responded with a significant increase in their Hb level, 6 of the 11 patients that were transfusion dependent enjoyed a complete abolition of BTR, and 12 patients enjoyed an improved quality of life, interpreted as a lower WHO PS score.

Five patients of the clinical trial reported in Mittelman et al., 1997, continued to receive rHuEpo for their anemia for several years. These patients all displayed increased Hb and, in general, were "doing very well" relative to the severity of their disease (high tumor mass). Interestingly, the patients continued to exhibit high serum paraprotein levels.

Based on these clinical observations and on the assumption that, at least in some of the patients, in addition to increasing Hb levels, Epo might be responsible for changing the biology and course of the disease (MM) itself, experiments according to the present invention were thus pursued with a murine model to study the possible non-erythroid or other biological effects of Epo on the course and biology of MM. For this purpose, we used the mineral-oil induced plasmacytoma in BALB/c mice, designated MOPC-315 tumor, a well-known murine model for the study of clinical and immunological aspects of human MM (Potter and Walters, 1973). Similarly to the human MM cells, the murine MOPC-315 tumor cells synthesize and secrete a monoclonal IgA (λ2) immunoglobulin, thereby providing a measurable tumor marker (serum myeloma component) during tumor progression. The in vivo effect of rHuEpo treatment on the growth of MOPC-315 tumor cells was studied in BALB/c mice. As shown in the examples hereinafter, tumor regression was strikingly observed in 30–60% of mice challenged with tumor cells and further treated for a short period with Epo, without tumor recurrence throughout a follow-up period of 3–7½ months. The event seems to be associated with the development of an effective antitumor immune response.

As used herein in the specification, "regressor mouse" or "regressor" refers to a mouse injected with tumor cells, followed by initial tumor growth and gross disappearance of the tumor cells after Epo treatment. "Progressor mouse" or "progressor" refers to a mouse injected with tumor cells, followed by continuous tumor growth irrespective of Epo treatment. "Null" mouse refers to a mouse in which no tumor take is observed after injection of tumor cells.

The observations with the MM patients and the mouse myeloma model constitute one specific embodiment but it is encompassed by the present invention the use of a medicament comprising erytropoietin for the treatment of any kind of neoplastic disease, excepting renal cell cancer.

As used herein in the specification and the claims, "erythropoietin" includes all types of erythropoietin, both natural and recombinant, as well as erythropoietin analogs showing erythropoietin activity, that are suitable for human administration such as the hyperglycosylated analogs and analogs having 1–14 sialic acid groups and changes in the amino acid sequence mentioned above. In one preferred embodiment, the erythropoietin is recombinant human erythropoietin (rHuEpo).

Any suitable route of administration of Epo such as intravenously (i.v.) or subcutaneously (s.c.), can be used according to the invention, but the s.c. route is preferred because of better distribution in the body and a better bioavailability. The Epo dose may be within the range of 5,000–20,000 U, preferably 10,000 U per injection (corresponding roughly to 150 U/kg). The protocol of administration will be determined by the physician according to the type of cancer, the severity of the disease, age and physical condition of the patient and other relevant parameters for each case. For example, in MM patients, a unit dose of about 10,000 U can be injected s.c. 3 times a week for about 4 weeks, followed by further therapy, if necessary. It should be noted that, according to the data accumulated from the anemia studies, patients with high response to Epo treatment are those with endogenous Epo level of less than 200 mU/ml (endogenous normal Epo level: 10–25 mU/ml; endogenous Epo level in anemic patients: higher than 100 mU/ml and in the level of hundreds or thousands mU/ml).

The invention will now be illustrated by the following non-limiting Examples.

EXAMPLES

Materials and Methods

Materials rHuEpo (EPREX) was obtained from Cilag, Schaffhausen, Switzerland. The murine tumors plasmacytomas MOPC-315 and MPC-11, chronic lymphocytic leukemia (CLL) BCL1, Lewis lung carcinoma 3LL, MCA-105 fibrosarcoma, K-1735 melanoma and the hybridomas GK 1.5 (producing anti-CD4 monoclonal antibody) and 53-6-7 (producing anti-CD8 monoclonal antibody), were purchased form the American Type Cell Culture (ATCC), Rockville, Md., USA. The C-26 colon carcinoma and M-109 lung carcinoma were kindly provided by Prof. E. Kedar (Hebrew University, Jerusalem, Israel), and 107–202 breast adenocarcinoma, 38C-13 pre B cell leukemia, 127C lymphosarcoma, and 17A-443 acute myeloid leukemia were established in our laboratory.

MOPC-315 Tumor Challenge

The mouse myeloma MOPC-315 was maintained in vivo by serial I.M inoculation into syngeneic female BALB/c mice aged 8 weeks. BALB/c mice were injected subcutaneously (s.c.) with $10^4$ cells in the abdominal area. Local tumor growth (2–5 mm diameter) was observed by day 11–13, gradually growing in size and causing death in 90–100% of mice by day 40–50. Subcutaneous rHuEpo treatment was started when a tiny palpable tumor appeared at the site of injection. Each mouse was numbered and the tumor growth rate of the individual mice (its diameter in mm) was measured by a vernier caliper. A follow-up of tumor size in individual mice was carried out every fifth day during Epo administration (lasting usually 4 weeks).

SDS Gel Electrophoresis (SDS-PAGE)

Sera from mice were diluted (1:1) in NaCl 0.9% and 2 μl of the diluted sera were resolved by 10% SDS-polyacrylamide gel electrophoresis. Protein bands were detected by Coomassie blue staining (0.05% v/v Coomassie brilliant blue R-250 (Bio-Rad) in 10% acetic acid, 50% methanol followed by destaining in 10% acetic acid, 20% methanol).

Western Blot Analysis

Western blot analysis was performed as previously described (Neumann et al., 1993). 2 μl of sera diluted 1:1 in 0.9% NaCl, were resolved on 10% SDS-PAGE. MOPC-315 immunoglobulin (20 μg) was loaded as a positive control. The gel was blotted onto nitrocellulose membrane filter, and probed with rabbit antibodies against mouse immunoglobulin λ light chain. Subsequently the blots were incubated with secondary antibody (donkey anti-rabbit IgG) coupled to horseradish peroxidase (HRP), and the bands were visualized using enhanced chemiluminescence (ECL) according to the manufacturer's instructions.

Example 1

Long-term rHuEpo Treatment of Multiple Myeloma (MM) Patients

In the study described in Mittelman et al., 1997, seventeen (17) patients with MM and anemia (Hb<11 g/dl) were enrolled in an open-label non-comparative study to test the serum Epo levels in anemic patients with MM, as well as to evaluate the efficacy and toxicity of rHuEpo in the treatment of anemia in these patients. The median age of the patients was 70 years (range 44–88), six were males and 11 females. All patients had stage II/III disease. Fifteen patients were on chemotherapy during the study period, 3 on the vincristine-adriamycin-dexamethasone (VAD) regimen and the remaining on oral melphalan and prednisone (MP) regimen.

The median pretreatment endogenous serum Epo level was 150 mU/ml (range 11–232). The serum Epo level was assayed as described in Mittelman et al., 1997.

Patients received subcutaneous injections of rHuEpo, 150 U/kg 3 times a week, on an outpatient basis. If no response was observed after 4 weeks, the dose was doubled. Oral iron (Slow-Fe, 160 mg exsiccated ferrous sulfate, Ciba-Geigy, Basel, Switzerland) was added. Therapy with rHuEpo was designed for 12 weeks, although 6 patients proceeded with rHuEpo treatment following the study termination. Rising of Hb levels beyond 14 g/dl during the study required a dose modification.

Complete response was defined as an increase (from baseline) of the Hb level (at week 12) by >2 g/dl, and/or complete abolishing of blood transfusion requirements (BTR). Partial response was defined as an increase of 1–2 g/dl in the Hb level and/or 50% reduction of BTR. Twelve patients (70.6%) achieved complete response and another patient (5.9%) showed partial response, which together gave a total response rate of 76.5%, based on intention-to-treat basis. The median Hb level rose from 9.4 g/dl (range 7.3–10.7) at study commencement to 12.5 g/dl (9.0–15.2) at week 12 (for those who completed the study).

Six patients continued rHuEpo treatment beyond the designed 12-week study period for 14–85 weeks and continued to maintain normal or near-normal Hb levels and to enjoy a good quality of life at a maintenance dose which is lower (15–50%) than the initial dose required to obtain a response.

According to the present invention, four of the patients of the above study, (Y. S., O. G., L. B. and T. S) and a new patient (M. B.) continued to receive rHuEpo for several years. These patients all displayed increased Hb and in general were "doing very well", relative to the severity of their disease. The characteristics of the 5 patients are summarized in Table 1.

These observations seemed to indicate that, at least in some patients, in addition to increasing Hb, Epo may change the biology and course of the disease. We thus assumed that the improved quality of life was not related only to the correction of the anemia. Since the common agent received by all 5 patients was Epo, and this in fact was the only therapy during most of the time of the follow-up reported here, we assumed that Epo, if administered at a certain dose for the appropriate period of time, may change the biology and course of the disease and lead to a longer survival, more than one would expect based on clinical criteria and considering the poor prognostic features of all these patients. The bone marrow plasma cells and especially the M-proteins, reflecting tumor mass, did not disappear in these patients, yet the course of the disease appeared to be stabilized, "frozen" or become latent and asymptomatic.

TABLE 1

Long Term rHuEpo In Multiple Myeloma Patients*

| PATIENT | | | | | Poor Prognostic | Other Rx for | Total●● duration | Duration of Epo only●● | |
|---|---|---|---|---|---|---|---|---|---|
| # | Initials | Age | Gender | MM Type | Features** | MM*** | of Epo (months) | (no chem) | Comments |
| 1 | YS | 59 | M | LC-L● | RF, CHF Amyloid. | MP | 64+ | 61+ | dialysis (July 1997) |
| 2 | OG | 44 | F | IgG-K | Very high tumor mass | See below♥ | 44+ | 42+ | M-spike >10 g/dL |
| 3 | LB | 68 | F | IgG-K | Hypercalcemia | MP, RT | 52+ | 52+ | |
| 4 | TS | 73 | F | IgG-L | RF | MP plasma | 43 | 40 | died in October 1997 of CRF |
| 5 | MB | 55 | M | IgG-L | Very high tumor mass | MP, RT VAD | 32+ | 32+ | numerous lytic lesions |

Notes:
*Data are summarized and updated as for April 1999
**Poor prognostic features in addition to anemia (see Durie & Salmon 1975; Bergsagel 1990).
***Other treatment modalities the patient received for MM during the course of the disease.
♥Patient 2, OG, received VMCP alternating with VBAP, followed by VAD and then HDC. For abbreviations - see below.
●Total Vs only: The total duration of rHuEpo administration (including periods when the patients received other treatment modalities for MM) as opposed to the duration the patient received rHuEpo as the only therapy. The + sign indicates that the patient was still on rHuEpo while summarizing these data (April 1999). Patients OG and LB have been on pamidronate too from mid 1998.
●●Abbreviations: LC — light chain; L — lambda; K — kappa; RF — renal failure; CHF — congestive heart failure; MP — melphalan + prednisone; VMCP — vincristine + melphalan + cyclophosphamide + prednisone; VBAP — vinblastine + BCNU + adriamycin + prednisone; VAD — vincristine + adriamycin + dexamethasone; HDC — high dose cyclophosphamide; RT — radiation therapy Based on these clinical observations, we then pursued with a murine model in an attempt to study possible non-erythroid or other biological effects of Epo on the course and biology of MM.

Example 2 rHuEpo Administration to Mice Challenged with MOPC-315 Tumor Cells Induces Tumor Regression Mice challenged with a syngeneic progressive growing myeloma ($10^4$ cells s.c.) were treated with rHuEpo by systemic administration. Tumor growth over the period of 2–2.5 weeks was similar in all mice and was followed by a decrease in tumor size in some Epo-treated mice culminating in a permanent and complete tumor regression in 30–60% of treated mice (compared to 0–10% in controls). Effects of different Epo regimens were tested. The results of four different representative experiments are summarized in Table 2.

In Experiment I, Epo treatment (30 U, injected s.c.) started 11 days following tumor cell challenge. Mice received daily injections for 5 days and, after 6 days interruption, further injections 3 times a week for 3 weeks. Most of the tumor-injected mice which did not receive Epo had died. This Epo treatment yielded 30% tumor regression and slightly prolonged the survival of the Epo-treated mice.

In Experiments II and III, the initial Epo treatment (its onset 13 or 11 days post s.c. tumor cell injection) was prolonged to 10 consecutive days followed by 3 weekly injections for another 2 weeks. In Experiment II, the effect of two doses of Epo (30 U or 100 U per injection) were tested. The incidence of tumor progression in mice injected with the high dose of Epo (100 U) was similar to that observed in the control group (14% and 10%, respectively). In contrast, in mice created with the lower dose of Epo (30 U per injection), tumor regression was observed in 60% of mice. In Exp. III tumor regression was observed in 40% of mice treated with 30 U Epo. This tumor regression was fully established at the time Epo treatment was terminated. Since then, no tumor recurrence in the regressor mice was observed throughout the follow-up period (7½ months in Exp. II and 3–4 months in Exps. III and IV) despite of being off Epo. It should be pointed out that spontaneous tumor regression in the control groups was usually between 0–10%.

In exp. IV various regimens were tested (10, 20 or 30 U per injection and 3 weekly injections for 4 weeks in comparison to 10 daily injections followed by additional 3 times weekly injections for 2 weeks). Significant tumor regression (50%) was observed only when the treatment schedule of Exp. II and III (30 U per injection) was followed. The same dose administered 3 times a week for 4 weeks was less effective (only 18% regression versus 9% spontaneous regression in the control group). The administration of lower Epo doses (10 U, 20 U) failed to interfere with tumor progression irrespective to time schedules of treatment. Epo treatment had no effect on the rate of tumor progression in these mice that did not respond to Epo treatment.

It can thus be summarized that the optimal rHuEpo treatment corresponds to Exp. II which involved daily subcutaneous injections of 30 U for 10 consecutive days followed by 3 times a week injections of the same dose for 2 additional weeks. Complete tumor regression was observed upon termination of Epo treatment and no myeloma relapse was observed during a follow-up period of 7½ months. Tumor progression in mice not responsive to Epo treatment (culminating in their death) was also observed at the same time or shortly after termination of Epo treatment (no decreased tumor growth rate was observed in these mice).

Figure 2:
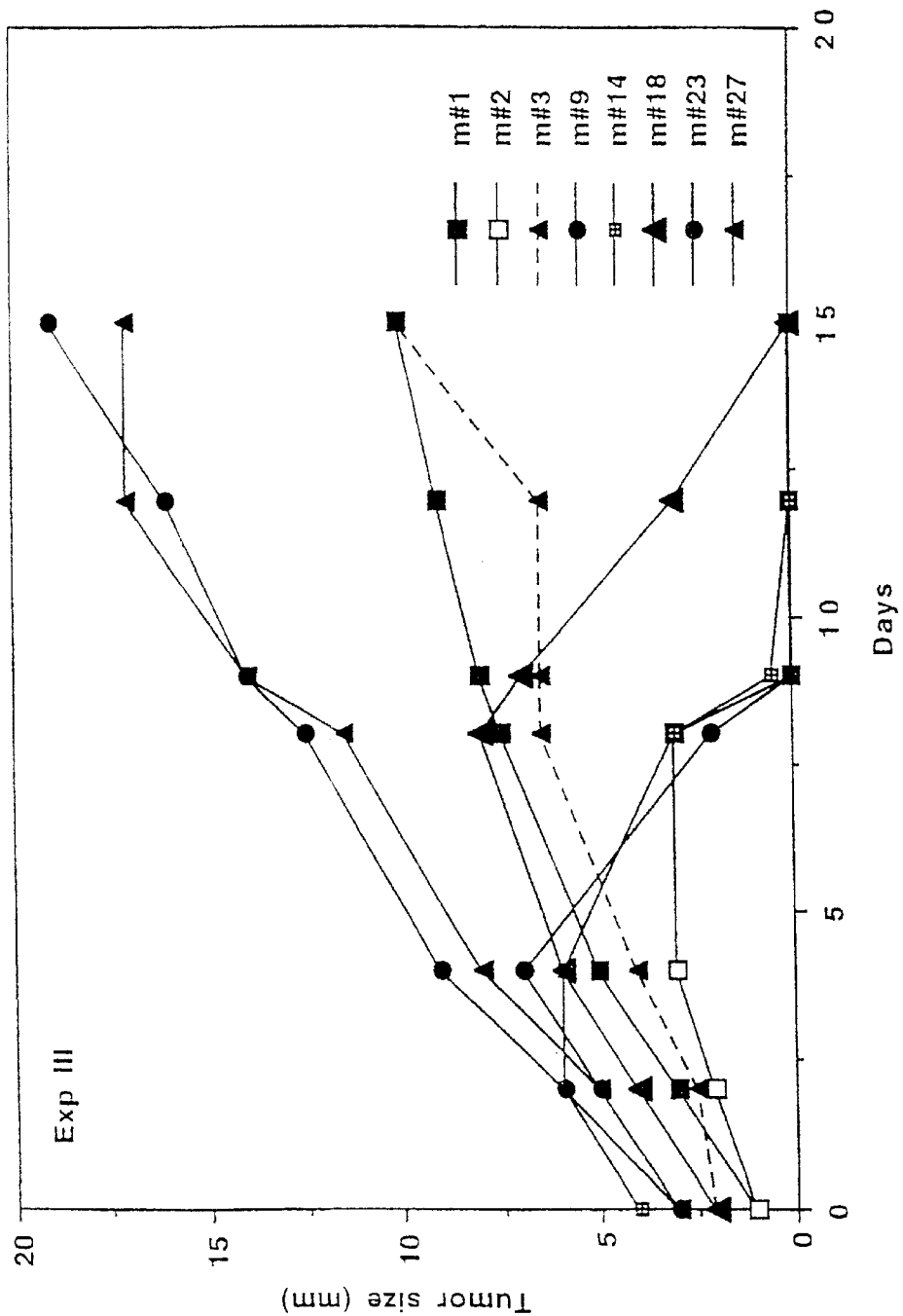
FIG. 2 shows the rate of tumor growth in progressor and regressor mice of Exp. III described in Example 2 herein. Mice # 1,2,3,9,14,18 were treated with rHuEpo (30 U). Mice # 23,27—controls.
Figure 3:
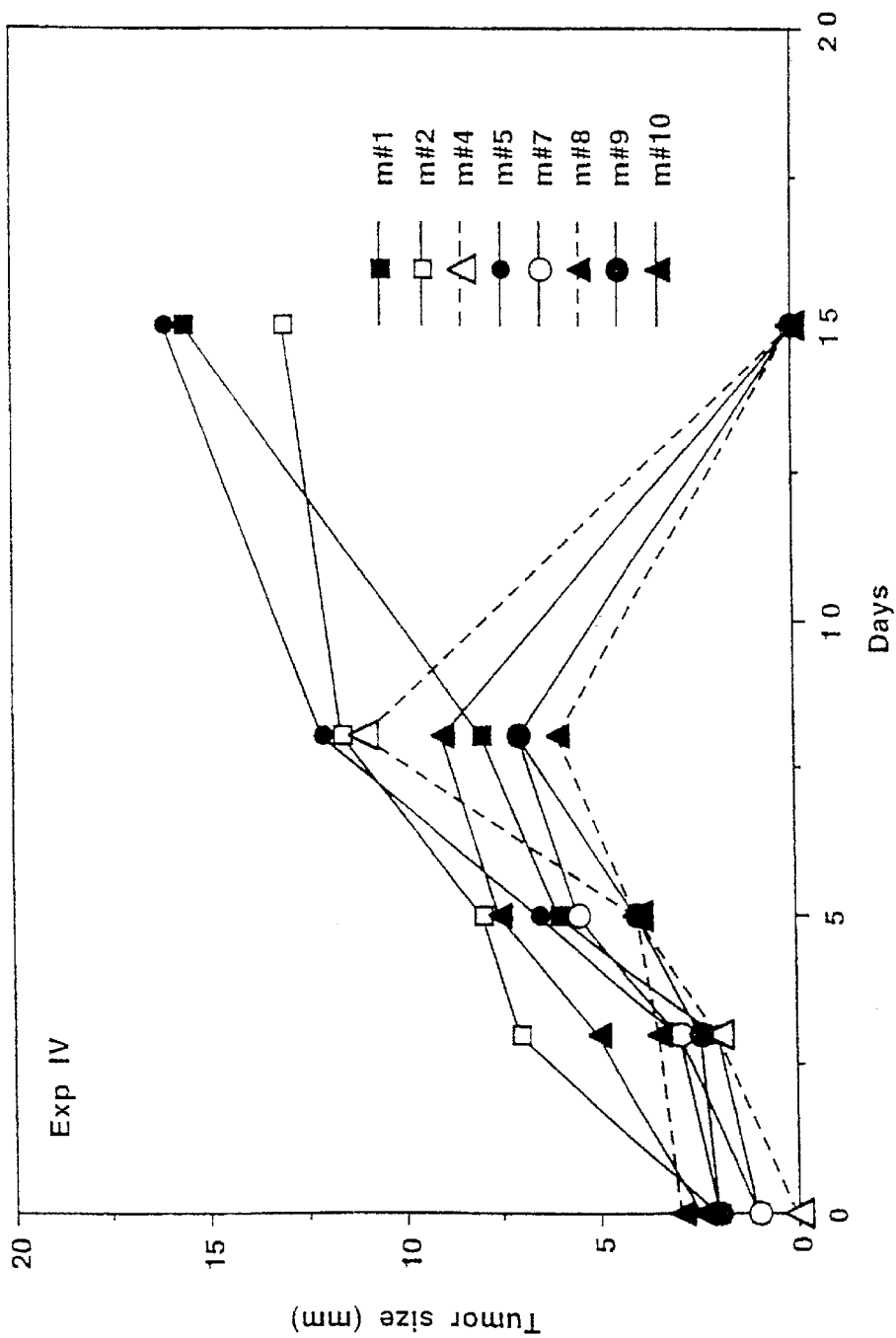
FIG. 3 shows the rate of tumor growth in progressor and regressor mice of Exp. IV described in Example 2 herein. Mice # 4,7,8,9,10—regressors following rHuEpo (30 U) treatment. Mice # 1,2,5—progressors among rHuEpo (30 U) treated mice.
Figure 4:
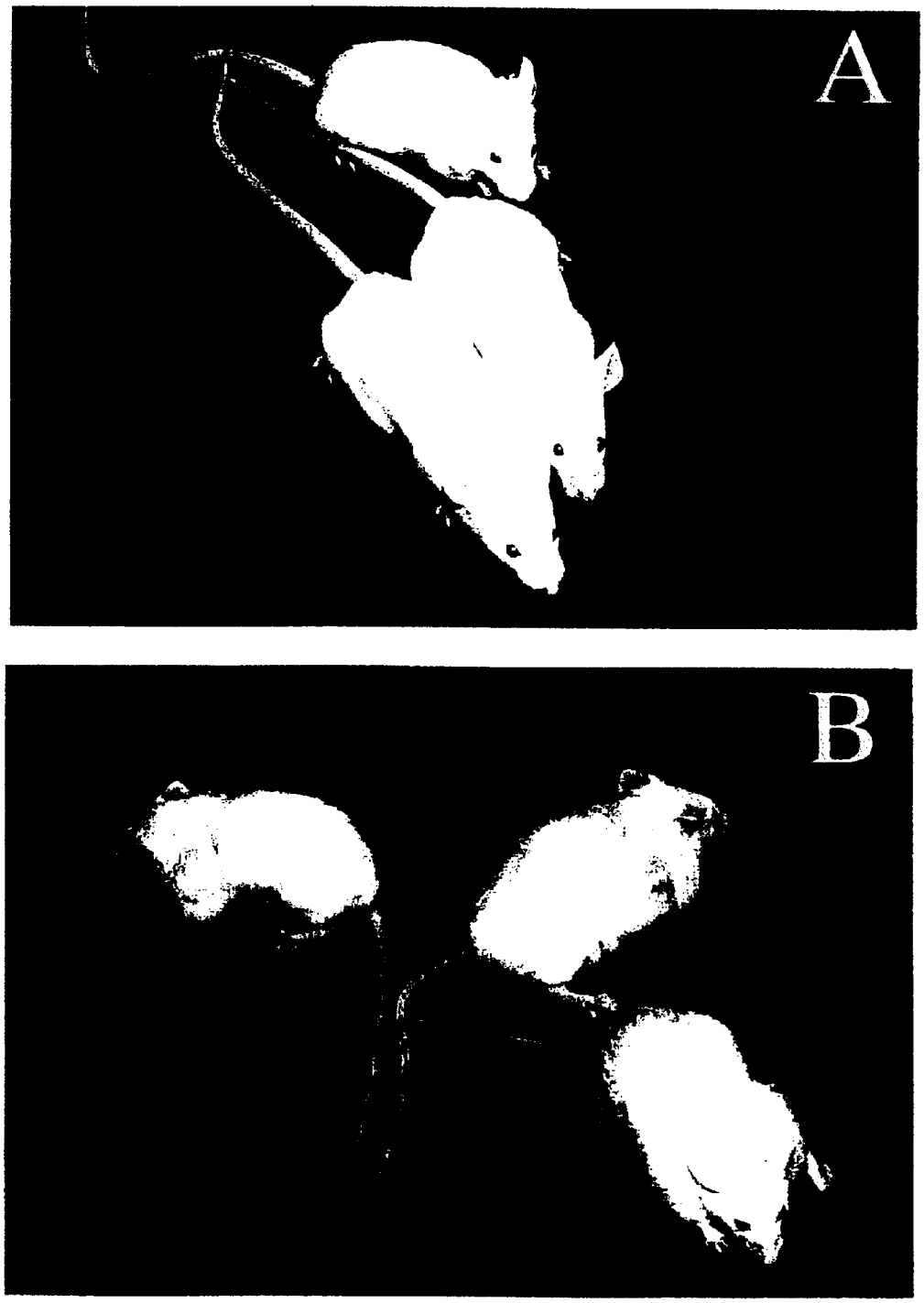
FIG. 4 illustrates the appearance of regressor (A) and progressor (B) mice following rHuEpo (30 U) treatment.

The dynamics of tumor growth in progressors and regressors in individual mice in the experiments II, III and IV is described in FIGS. 1–3, respectively. Usually up to six days from Epo administration (17–18 days since tumor cell challenge) no variations in tumor growth rates among progressors or regressors were observed. By 12–15 days, tumor size clearly drops in mice responding to Epo treatment, leading to final tumor regression, while in non-responders tumor size increases culminating in the death of the mice. FIG. 4 shows the difference in the appearance of regressors (A) and progressors (B): tumor growth is clearly seen in B.

TABLE 2

Myeloma regression following treatment with erythropoietin

| | | Tumor progressors | |
| --- | --- | --- | --- |
| Experimental treatment | Incidence of tumor regressor | Incidence | Latency (days) |
| Exp. I | | | |
| MC$^{b11d}$ 30u Epo$^c$ daily × 5$^{6d}$ 3 times a week for 3 wks. | 3/10 - 30% | 7/10 - 70% | 40 ± 3.2 |
| MC - control | 1/9 - 11% | 8/9 - 89% | 33 ± 3.7 |
| Exp. II | | | |
| MC$^{13d}$ 30u Epo daily × 10 → 3 times a week for 2 wks. | 6/10 - 60% | 4/10 - 40% | 47 ± 12 |
| MC$^{13d}$ 100u Epo daily × 10 → 3 times a week for 2 wks. | 1/7 - 14% | 6/7 - 85% | 4 ± 13 |
| MC - control | 1/10 - 10% | 9/10 - 90% | 40 ± 6 |
| Exp. III | | | |
| MC$^{11d}$ 30u Epo daily × 10 → 3 times a week for 2 wks. | 4/10 - 40% | 6/10 - 60% | 42 ± 10 |
| MC - control | 1/9 - 11% | 8/9 - 89% | 39 ± 3 |
| Exp. IV | | | |
| MC$^{12d}$ 30u Epo daily × 10 → 3 times a week - 2 wks. | 5/10 - 50% | 5/10 - 50% | 37 ± 3.4 |
| MC$^{12d}$ 30u Epo daily × 10 → 3 times a week - 4 wks. | 2/11 - 18% | 9/11 - 82% | 38 ± 3 |
| MC$^{12d}$ 20u Epo daily × 10 → 3 times a week - 2 wks. | 0/11 — | 11/11 - 100% | 34 ± 1.8 |
| MC$^{12d}$ 20u Epo daily × 10 → 3 times a week - 4 wks. | 0/10 — | 11/11 - 100% | 36 ± 3.1 |
| MC$^{12d}$ 10u Epo daily × 10 → 3 times a week - 2 wks. | 0/11 — | 11/11 - 100% | 38 ± 3.2 |
| MC$^{12d}$ 10u Epo daily × 10 → 3 times a week - 4 wks. | 1/11 - 9% | 10/11 - 90% | 41 ± 2.8 |
| MC - control | 2/31 - 6% | 29/31 - 93% | 37 ± 3.4 |

Notes:
$^a$latency - means interval (survival) in days of progressor mice from tumor inoculation till death.
$^b$MC — myeloma cells - 10$^4$ injected subcutaneously.
$^c$Epo regimen: rHuEpo (Eprex, Janssen/Cilag) was injected subcutaneously.

Example 3

Paraproteins in the Serum of Tumor MOPC-315 Bearing Mice

Myeloma is characterized by a clonal proliferation of bone marrow plasma cells secreting a paraprotein which can be detected in the serum, thereby serving as a tumor cell marker. The mouse myeloma MOPC-315 cells synthesize and secrete immunoglobulin IgA with $\lambda 2$ light chain and an $\alpha$ heavy chain.

Serum paraproteins in myeloma regressor and progressor mice and control mice were detected using Coomassie brilliant blue staining of serum proteins resolved by SDS-polyacrylamide gel electrophoresis. Sera from myeloma regressor or progressor mice were collected after termination of Epo treatment in comparison to sera from normal BALB/c mice or BALB/c mice treated with Epo without previous tumor cell challenge. In the sera of both progressor and regressor mice a distinctive 27 kD band was observed (much fainter in sera of control healthy mice).

Figure 5:
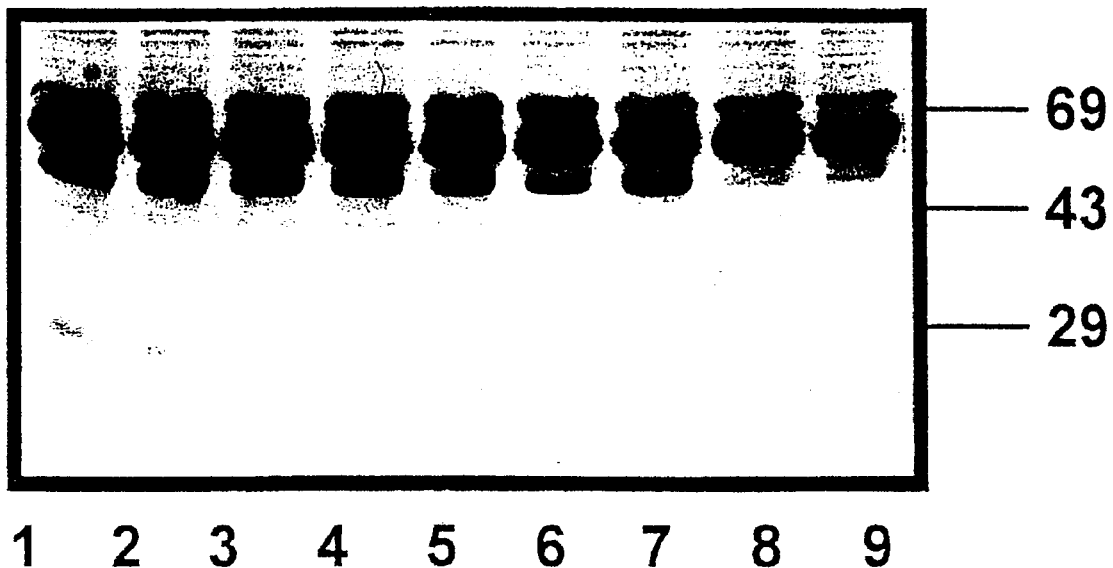
FIG. 5 shows that progressor as well as regressor mice express a distinctive 27 kD paraprotein band detected in the serum. Two µl of mice sera diluted 1:1 in 0.9% NaCl were resolved on 10% SDS-PAGE. Molecular weight markers in kD are indicated on the right. Lanes 1–2—regressor mice; lanes 3–4—treated progressor mice (30 U and 20 U EPO); lanes 5–6—untreated progressor mice; lane 7—mouse injected with the tumor but showing no visible tumor; lane 8—mouse not injected with the tumor and treated with 30 U EPO; lane 9—normal control.

We then analyzed sera of 40 mice injected with $10^4$ MOPC-315 cells s.c. and after 12 days treated with either Epo or Epo diluting solution only. Individual marked mice were bled twice (from the orbital vein)—17 days after tumor cell challenge, during the ongoing Epo treatment and 2 weeks later, towards termination of Epo treatment. At that stage we could clearly define regressor mice responsive to Epo treatment versus non-responsive progressor mice and also some "null" mice—where tumor takes were not observed from start. Sera from myeloma-bearing mice that did not receive further Epo treatment (including also few "spontaneous" regressors) and sera from control mice were also included in this survey (FIG. 5). Seventeen days after myeloma challenge we observed in all sera tested a prominent 27 kD band which was barely detected in sera of control mice that were not challenged with tumor cells. The deviation to progressors and regressors following Epo treatment did not affect the presence of the 27 kD band in the sera. Thus, the 27 kD band correlated only with the initial tumor cell injection into BALB/c mice and not with disease severity. Even in the serum of "null" mice the 27 kD protein band was observed.

FIG. 5 represents the profile of serum proteins in Epo regressors (lanes 1–2), Epo progressors (lanes 3–4), progressors in controls (without Epo treatment, lanes 5–6), a "null" mouse (lane 7), a non-injected BALB/c control mouse (lane 8) and a BALB/c mouse injected only with Epo (no myeloma cells, lane 9).

Figure 6:
FIG. 6 shows the 27 kD band in sera of regressor mice 2 weeks, and 2,4 and 7 months after tumor challenge. Lane 1—normal control; lanes 2–3—2 weeks post-regression; lanes 4–5—2 months; lanes 6–7—4 months; lanes 8–9—7 months post-tumor cell challenge.

We also tested sera from Epo-treated regressor mice 2,4 and 7 months after tumor regression, throughout this period no signs of tumor relapse were observed and the mice looked grossly normal. Tests of representative sera samples of these mice are illustrated in FIG. 6. All sera displayed the 27 kD protein, thereby suggesting the presence of "dormant" tumor cells in the myeloma regressor mice that continue to produce and secrete paraproteins.

Malignant cell arrest in different organs (including spleen) of mice bearing subcutaneous transplanted tumors including MOPC-315 was demonstrated years ago in the laboratory of one of the present inventors (Haran-Ghera et al., 1981). Sequestration of tumor cells derived from the transplanted tumor was indicated already within 3 to 7 days after tumor graft, shortly before or after early palpable outgrowth of the primary tumor was observed. We therefore assumed that spleens from the regressor mice might be carriers of dormant MOPC-315 tumor cells.

To test this possibility according to the present invention, we splenectomized regressor mice (4½ months after myeloma cell challenge) and transplanted spleen cell suspension or whole spleens into syngeneic recipients. Spleen suspensions from 7 individual regressors were prepared—half spleen cell suspension was injected i.v. into normal syngeneic BALB/c mice and the other half into irradiated BALB/c mice (2 hr following their exposure to 400r whole body irradiation).

Figure 7:
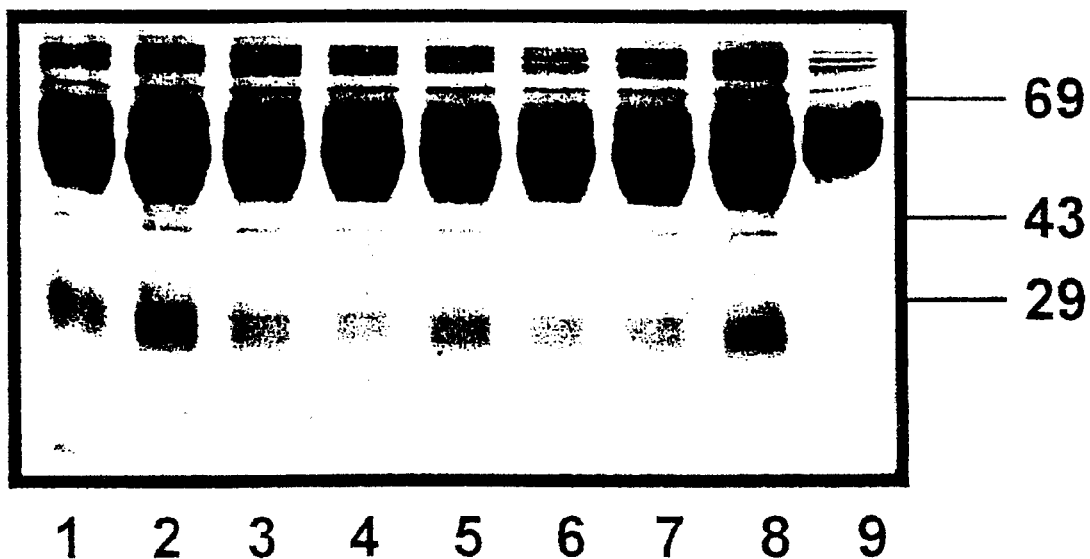
FIG. 7 gives evidence of "dormant" tumor cells in spleens of regressor mice. Since the 27 kD band is present in their sera, spleen cell suspensions were prepared from 7 individual spleens removed from regressor mice. Half spleen cell suspension was injected (i.v.) into a normal syngeneic BALB/c mouse and the other half into an irradiated BALB/c mouse. Lanes 1–2—represent sera from irradiated spleen cell recipient and normal recipient of the same individual spleen. Lanes 3–4, lanes 5–6 and lanes 7–8—similar presentation of the spleen transferred into irradiated or normal recipient. Lane 9—serum from a normal non-injected BALB/c mouse.

Fifty and 75 days after spleen-cell transfer, 2/7 irradiated spleen cell recipient mice developed tumors and no tumors were observed in the normal recipients. The regressor spleen donors looked grossly normal 7½ months after the initial myeloma cell challenge. Sera analysis of spleen cell recipients revealed presence of the 27 kD protein in all spleen cell recipients (see FIG. 7). In another experiment, whole spleens removed from 8 regressor mice were transplanted s.c. into normal recipients. 3/8 grafted spleens developed local tumors at the site of transplantation. These spleen recipients were bled 10 days and 3 weeks after spleen grafts and their sera were shown to be positive for the 27 kD protein band (FIG. 7).

Figure 8:
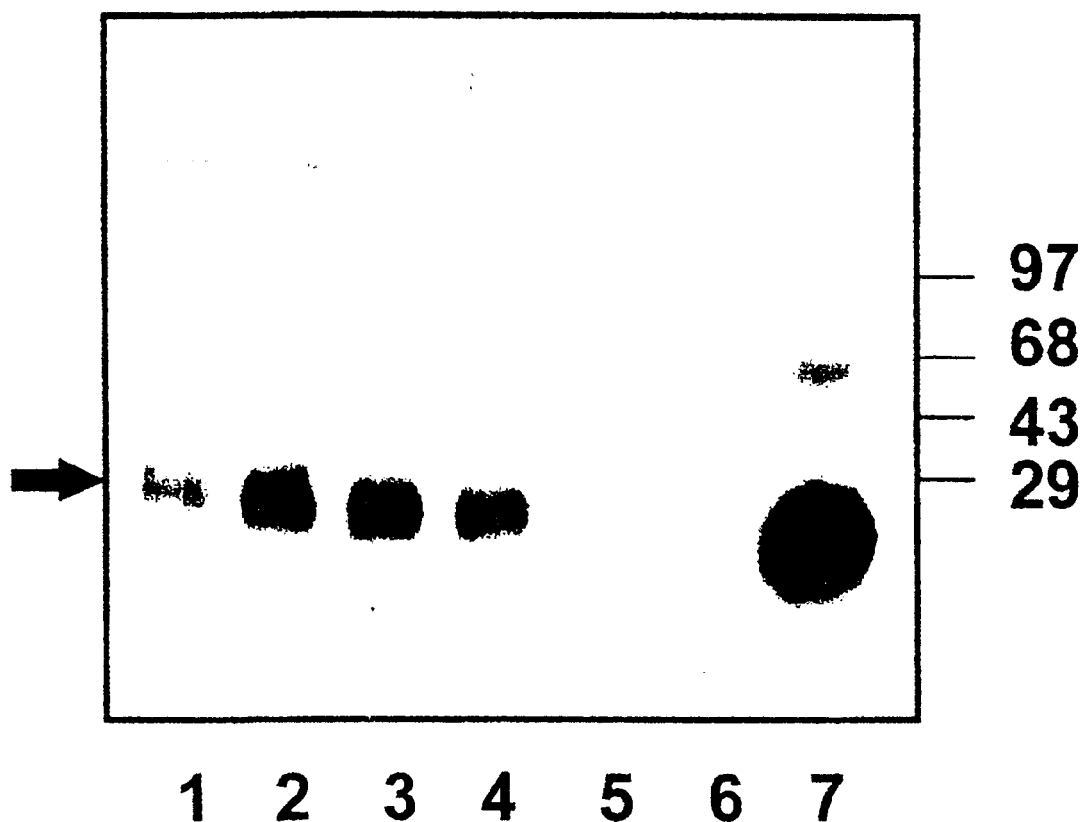
FIG. 8 depicts a Western blot analysis showing that the 27 kD band corresponds to the immunoglobulin λ light chain: lanes 1–2—serum from a mouse grafted with a spleen from a regressor mouse bled 10 days and 3 weeks after grafting; lanes 3–4—sera from 2 regressor Epo-treated mice; lanes 5–6—sera from control non-injected healthy mice; lane 7—control. IgA secreted from MOPC-315 cells were resolved in 10% SDS-PAGE, and the gel was subsequently immunoblotted with λ immunoglobulin light chain antibodies.

The 27 kD band which characteristically appears in sera of mice injected with MOPC-315, probably represents the $\lambda$ light chain of the IgA immunoglobulin secreted by MOPC-315 myeloma cells. To confirm this identification, sera from 2 regressor Epo-treated mice (FIG. 8, lanes 3,4), from a mouse grafted with a spleen from a regressor mouse and bled 10 days after grafting (lane 1) and 3 weeks after grafting (lane 2) (both bleedings from the same mouse), sera from control non-injected healthy mice (lanes 5,6) and control IgA secreted from MOPC-315 cells (lane 7) were resolved in 10% SDS-PAGE, and the gel was subsequently immunoblotted with anti-$\lambda$ immunoglobulin light chain antibodies. As can be seen in FIG. 8, shortly (10 days) after grafting a healthy mouse with a spleen from a donor regressor mouse, the 27 kD band reacted with the anti-$\lambda$ light chain antibodies (lane 1) and the signal was more intense (approximately 2 fold) than that observed in the sera of control mice (lanes 5 and 6). A significantly more intense 27 kD band was observed in the serum of this mouse 2 weeks later (lane 2), indicating that the myeloma cells had proliferated and the amount of secreted IgA increased (similar levels to those in sera of Epo-treated regressor mice (lanes 3–4). The 27 kD band migrated similarly to the corresponding band observed in the lane of the control antibody from MOPC-315 IgA (lane 7), unequivocally establishing it as the immunoglobulin $\lambda$ light chain.

Thus, according to these results, identification of paraproteins in sera of myeloma-bearing mice was found to be associated with the presence of tumor cells in these mice. A 27 kD protein band was observed in all mice challenged with myeloma cells irrespective to whether these cells ultimately progressed to lethality or regressed permanently. The 27 kD protein band was shown by Western blot analysis with anti-$\lambda$ immunoglobulin light chain antibodies to unequivocally correspond to the immunoglobulin $\lambda$ light chain.

The presence of "dormant" tumor cells in spleens of regressor mice was demonstrated by transplantation studies. Paraproteinemia in sera of all spleen-cell recipients and the emerging of few tumors developing in spleen recipients clearly indicate that the course of the disease following Epo treatment is under proliferation arrest (in a "dormant state").

Example 4

Hemoglobin (Hb) Levels Affected by Epo Treatment of BALB/c Mice

Figure 9:
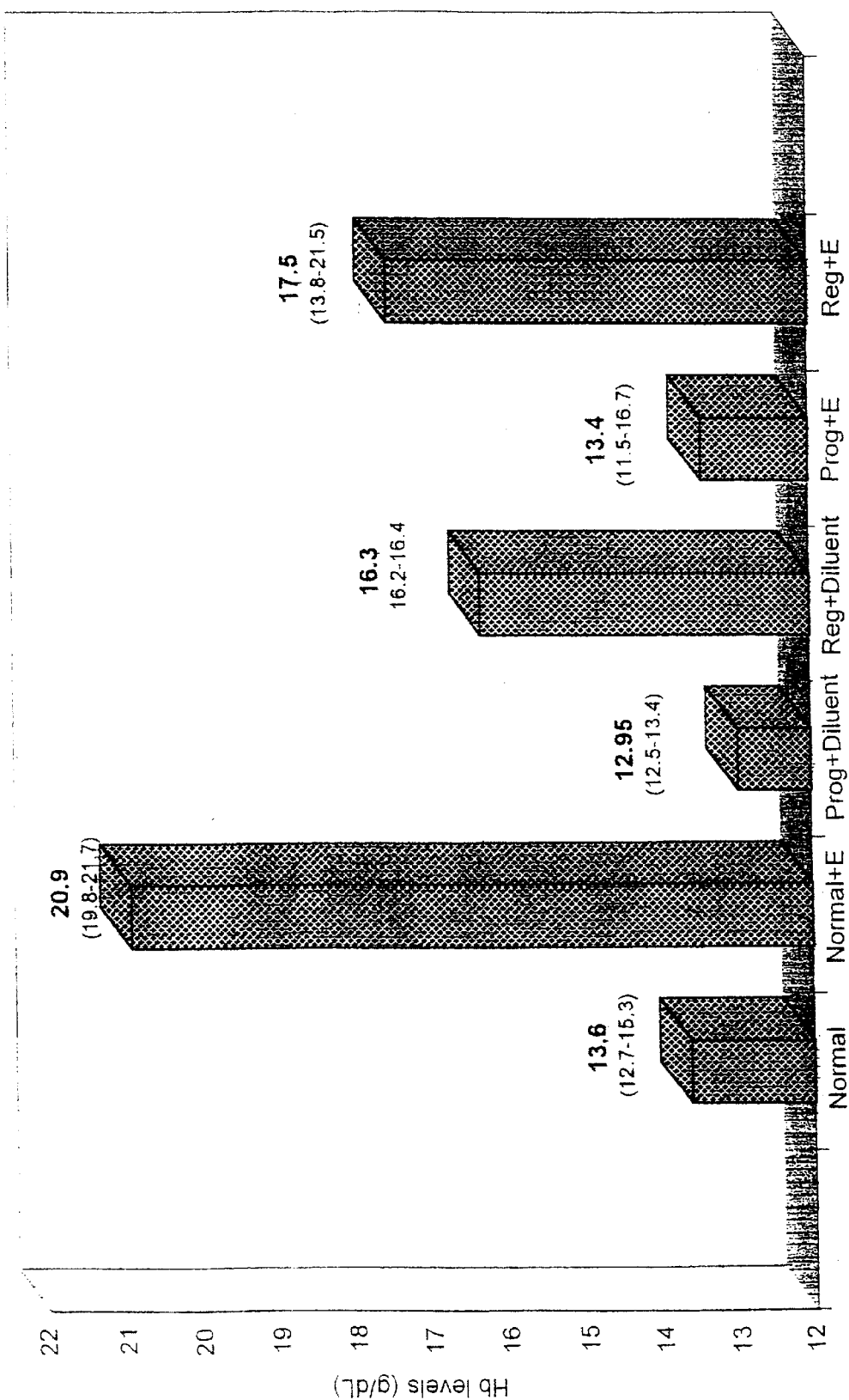
FIG. 9 shows hemoglobin (Hb) levels in normal BALB/c mice; normal mice injected with rHuEpo (E); progressor or regressor mice injected only with the Epo diluent (no Epo treatment); progressor mice not responsive to rHuEpo treatment and regressor mice following Epo treatment.

Hb levels were measured in normal control mice as well as in myeloma-bearing mice with or without Epo treatment, deviating into regressor and progressor mice (FIG. 9). Hb level in normal BALB/c mice ranged between 12.7–15.3 g/dl (mean 13.6). Normal mice treated with Epo showed elevated Hb levels (19.8–21.7 g/dl, mean 20.9). Among regressors treated with Epo, 7/9 mice tested showed elevated levels ranging from 17–21.5 g/dl (mean 18.4), and 2/9 had lower levels, close to normal values (13.8 and 14.5). Hb levels in 2 spontaneous regressors (myeloma-bearing mice injected with diluent) were 16.2 and 16.4 g/dl. In progressor mice treated with Epo, in 9/11 tested blood samples (taken from mice carrying a large tumor mass) Hb levels ranged from 11.5–13.4 g/dl (mean 12.6) whereas in 2/11 progressors that carried a small tumor load the levels were 16.3 and 16.7 g/dl. In 2 progressors treated only with diluent the Hb levels were 12.5 and 13.4 g/dl. Thus, the response of mice to Epo treatment is similar to that observed in humans. Epo increases Hb levels in normal mice. Tumor regression following Epo treatment is also associated with elevated Hb, whereas in Epo-treated myeloma progressors Hb levels remain low.

Example 5

Regressor Mice Resist Rechallenge with Second Tumor of the Same Type

The experiments described in Examples 2–4 above indicate that administration of Epo to tumor-bearing mice triggers immune responses that affect tumor regression. Anti-tumor immune responses seem to contribute to tumor regression and maintenance of tumor dormancy. Regressor mice (being in this state for several months) were rechallenged s.c. with $10^4$ MOPC-315 cells and resisted this second tumor cell challenge in contrast to normal control mice that developed 100% tumor takes 10–14 days after challenge (not shown).

Figure 10:
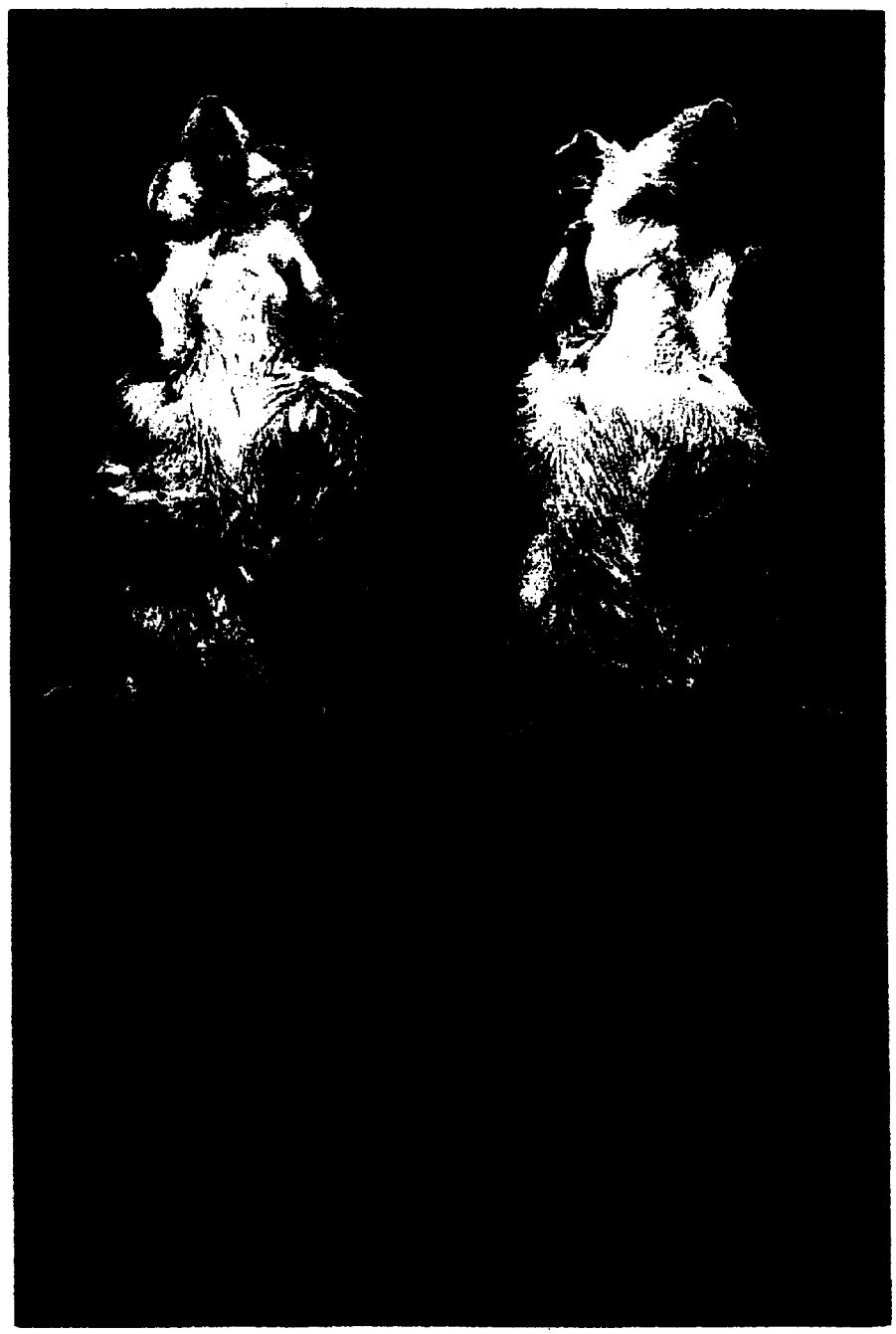
FIG. 10 shows a control mouse bearing both MOPC-315 and MPC-11 myeloma tumors (left) and a regressor mouse carrying only myeloma MPC-11 tumor on the right ventral surface (right).

The specificity of this immunological triggered resistance was further demonstrated by challenging regressor mice bilaterally: on the left ventral surface with MOPC-315 cells, and on the right ventral surface with tumor cells from an unrelated myeloma (MPC-11, induced in BALB/c mice as described in Materials and Methods for MOPC-315). Both tumors grew progressively in control BALB/c mice.In contrast, the MOPC-315 growth was rejected in 7/7 regressor mice whereas MPC-11 grew progressively in these same hosts. FIG. 10 shows a control mouse bearing both MOPC-315 and MPC-11 myeloma tumors (left) and a regressor mouse carrying only myeloma MPC-11 tumor on the right ventral surface (right).

These results indicate that treatment with Epo promotes the development of an effective anti-tumor immune response and suggest that tumor regression induced by Epo renders these mice resistant to growth of a second myeloma cell challenge of the same type, thereby suggesting the built-up of an anti-tumor immune response responsible for tumor rejection.

Figure 11:
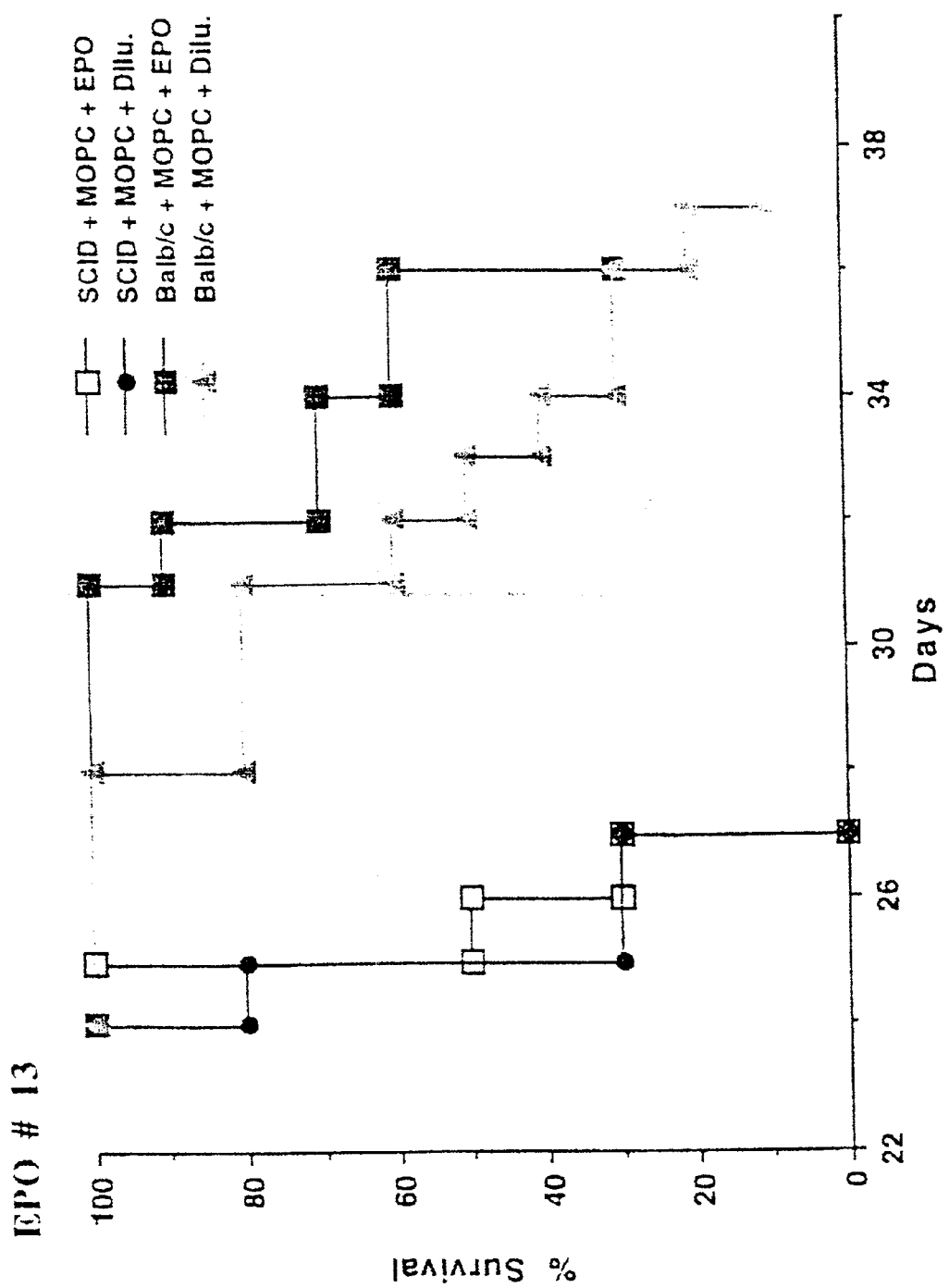
FIG. 11 shows the lack of response of scid mice to Epo treatment following tumor challenge (MOPC-315). 100% of mice died within 25–27 days in comparison to 50% tumor regression in the control group.
Figure 12:
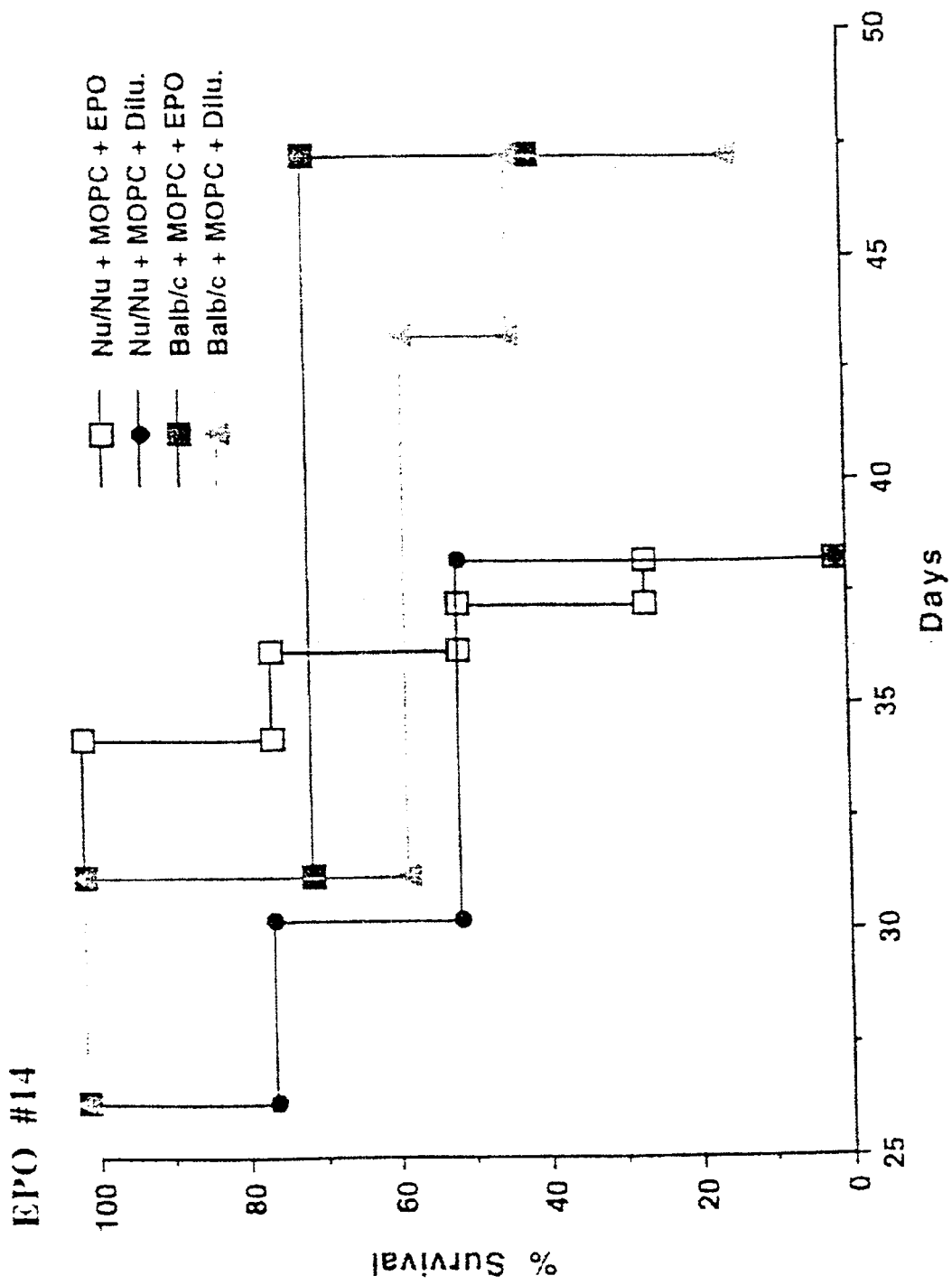
FIG. 12 shows abolishment of the curative effect of Epo treatment in nude mice challenged with MOPC-315 myeloma cells in comparison to control mice (40% undergoing tumor regression in contrast to 100% tumor development in Epo-treated nude mice).

Further experiments were carried out with Scid mice that are immunologically impaired (both cell-mediated and humoral immune responses)and with nude mice (cell-mediated impaired immune response), and both were found to be non-responders to Epo treatment following $10^4$ MOPC-315 cell challenge. In both the Epo and control group, all scid and nude mice died at the same time, within 24–26 days post-tumor cell challenge (FIGS. 11–12). In the control group (normal BALB/c mice) Epo treatment resulted in 30–40% tumor regression.

Example 6

Figure 13:
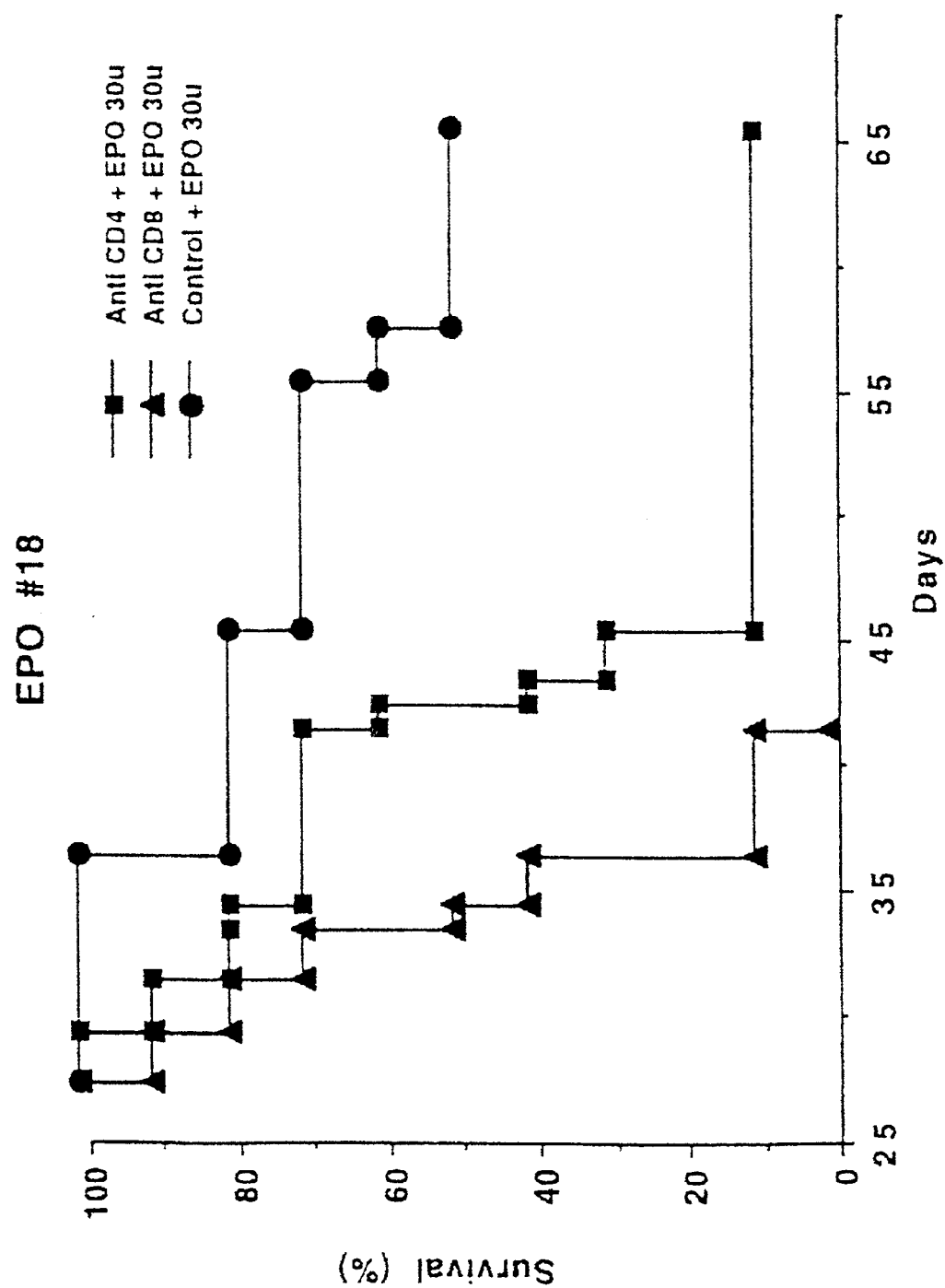
FIG. 13 shows the phenotype of the T-effector cells involved in tumor regression. Depletion of $CD8^+$ T cells abrogated the response of mice challenged with MOPC-315 myeloma cells (100% tumor development versus 40% tumor regression in the control group).
Figure 14:
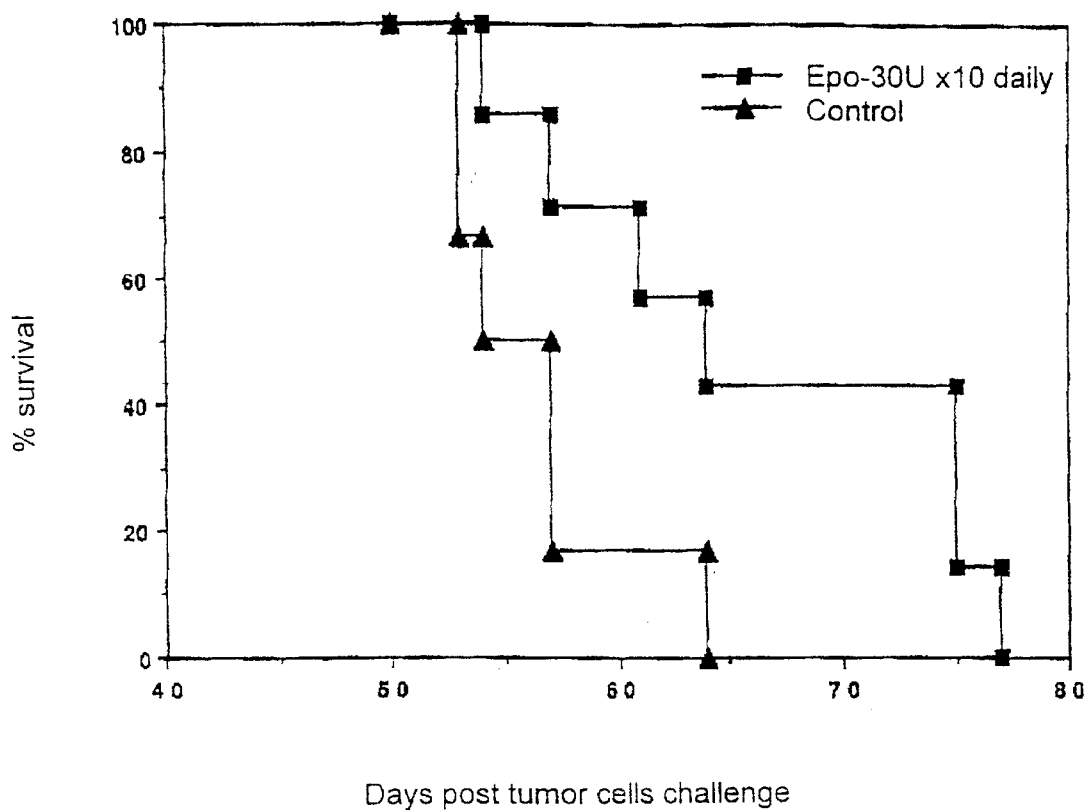
FIG. 14 shows the effect of administration of Epo on the survival of 3LL lung carcinoma-bearing mice (squares) in comparison to untreated control mice (triangles).

Tumor Regression in Epo-treated Tumor-bearing Mice is Mediated by; CD8$^+$ T-effector Cells To further elucidate the phenotype of tumor-specific effector cells, we tested whether depletion of CD4$^+$ or CD8$^+$ T cells would abrogate the ability of mice to respond to Epo treatment following tumor cell challenge. In mice treated with antibodies to CD8$^{30}$ cells, thereby eradicating all CD8$^+$ cells, no response to Epo treatment was observed and tumor growth was actually enhanced (not shown). In mice treated with antibodies to CD4$^+$ cells, thereby eradicating all CD4$^+$ cells, less eradication of Epo treatment on tumor regression was observed. In the control group, Epo treatment caused tumor regression in 50% of the treated mice (FIG. 13).

These data indicate that Epo treatment of tumor-bearing mice promotes the generation of Thy-1$^{30}$ CD8$^+$ T-effector cells that play a pivotal role in tumor regression in vivo in mice challenged with MOPC-315 myeloma tumor cells and further treated with Epo.

Example 7

Effect of Epo Treatment in Mice Bearing Different Tumors

The following tumor cells can be injected in mice according to the protocol described in Materials and Methods for myeloma MOPC-315: breast tumor using 107–202 adenocarcinoma cells, colon tumor using C-26 colon carcinoma cells, lung tumor using M-109 or 3LL lung carcinoma cells, chronic lymphocytic leukemia (CLL) using BCL1, melanoma K-1735, MCA-105 fibrosarcoma, 38C-13 pre B cell leukemia, 127-RadLV T-lymphosarcoma, 17A-443-acute myeloid leukemia and 17E-200 B-cell lymphoma. The tumor-bearing mice are then treated with Epo as described in the previous examples.

Preliminary Results

1) C57Bl/6 mice were challenged with lung adenocarcinoma 3LL cells, and thereafter treated with Epo following the myeloma protocol, namely 10 daily injections of 30 U Epo s.c. followed optionally by three weekly injections for additional 4 weeks. As shown in FIG. 11, a delay was observed in the survival of the 3LL tumor-bearing mice: 50% of the control mice died 54 days after the initial tumor cell challenge while 50% of the 3LL tumor-bearing mice treated daily for 10 days with 30 U Epo survived 75 days.

Figure 15:
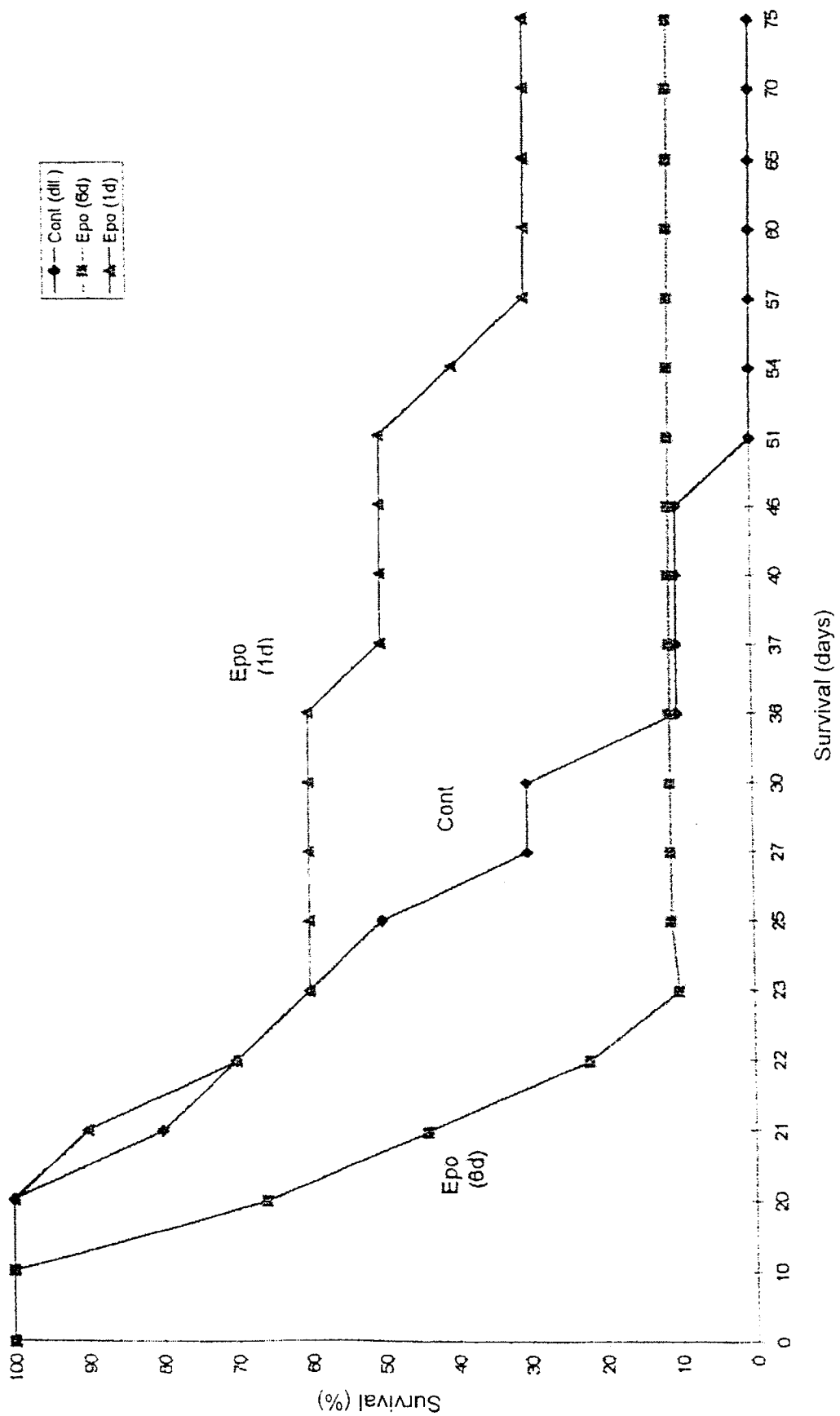
FIG. 15 shows the effect of Epo treatment initiated 1 day following tumor cell challenge on the survival of colon adenocarcinoma-bearing mice in comparison to initiating Epo treatment 6 days after tumor cell challenge or the control group.

2) BALB/c mice were challenged s.c. with C-26 colon carcinoma tumor cells. Epo administration starting one day following tumor cell challenge prolonged markedly the survival of tumor-bearing mice (30% survived for 100 days compared to 90% death in the control group at 36 days). Epo administration starting on day 6 following tumor cell challenge actually enhanced tumor growth (90% death at 23 days, as shown in FIG. 15).

Discussion

Our clinical observation suggests that at least in some myeloma patients Epo also induces a longer and more stable course of the disease (see Example 1, Table 1). The possible effects of exogenous Epo administration on the development of the disease was tested on a murine myeloma model, and showed indeed that mice challenged with a progressively growing myeloma and treated with Epo for a relatively limited short period, exhibited complete tumor regression in 30–60% of the treated mice using the optimal dose of Epo regimen. Compared effects of Epo doses (5–100 U) on tumor growth rate, using similar injection schedules, revealed that there is a dose threshold: in mice responsive to exogenous Epo administration, optimal tumor regression was achieved with a certain regimen (30 U daily s.c. injections for at least 10 days, starting Epo treatment when a small palpable tumor occurs). The maintenance of tumor regression was independent on further Epo administration. In mice shown to be non-responders to Epo treatment, no effect on the progressive tumor growth rate was observed; thus it appears that Epo acts as an "all or none" factor.

Anemia associated with human cancer is at least partially due to a relative deficiency of Epo and exogenous Epo can correct the anemia. There is a correlation between baseline endogenous serum Epo level and the response to rHuEpo treatment. Responders to Epo have usually a low Epo level (below 200 U/l) in comparison to that of non-responders. Thus, serum Epo level above 200 U/l is a possible predictor for resistance to Epo therapy. Similarly, the therapeutical response to Epo in mice involves rise in blood Hb concentration (FIG. 9). In Epo-responsive mice, tumor regression is observed along with increase in Hb level, in contrast to unchanged levels of Hb in mice unresponsive to Epo treatment.

Myeloma is a well-suited study model, because it contains a continuously available measurable tumor marker with which to examine possible interactions between the basic disease and its associated anemia. In our patients responding to Epo treatment, improvement from anemia coincided with a longer and stable course of disease in spite of the presence of serum myeloma paraproteins, indicating a dominantly stable tumor load. Similarly, in sera of regressor mice we observed the 27 kD protein band that corresponds to the immunoglobulin λ light chain secreted by myeloma cells despite disappearance of the visible tumor. Sequestration of myeloma cells to different organs in the regressor mice, including the spleen, has been demonstrated by transplantation studies. Transfer of spleen cells into syngeneic normal or irradiated recipients resulted in myeloma development in some mice; sera from all the spleen cell recipients contained the 27 kD protein band, thereby indicating the presence of "dormant" tumor cells in the myeloma regressor mice that continue to secrete paraproteins. Thus, the course of the disease following Epo treatment is under proliferation arrest (in a dormant state). Our observations in the experimental model coincide with similar observations concerning the Epo-treated patients (see Table 2). The bone marrow plasma cells and especially the myeloma proteins (reflecting tumor mass) did not disappear in the Epo-treated patients, yet the course of the disease appears to be stabilized, "frozen" or become latent and asymptomatic.

Studies on the biological mechanisms involved in Epo-triggered tumor regression according to the present invention suggest that anti-myeloma immunological reactivity is involved in tumor regression and maintenance of tumor dormancy. A series of experiments demonstrated that anti-tumor immune reactivity was associated with Epo-induced regression of tumors. Regressor mice rechallenged with the same tumor cells (MOPC-315) resisted the growth of this second challenge. Thus, memory to the tumor antigen was established in these regressors. The specificity of this immunological triggered resistance was also demonstrated (FIG. 10).

The involvement of T cells in Epo-triggered tumor regression was indicated by comparing the response of normal, scid or nude mice (immunologically impaired) to Epo treatment following tumor cell challenge. The efficacy of Epo treatment was markedly reduced in the immune impaired mice. Both in scid and nude mice there was no response to Epo treatment (FIGS. 11, 12). All Epo-treated mice developed tumor in comparison to 40% tumor regression in Epo-treated normal control mice.

These experiments rule out the possibility that Epo has a direct cytotoxic or cytostatic effect since no effect was observed in the above described T-cell depleted mice. Further studies concerned with the phenotype of the tumor effector cells indicated that the depletion of $CD8^+$ T cells abolished the curative effect of Epo. Tumor regression in vivo is mediated by $CD8^+$ effector cells and Epo treatment of tumor-bearing mice seems to promote the generation of these effector cells thereby augmenting the generation of effective anti-tumor response. In preliminary tests, we observed an increase in the number of hematopoietic progenitor cells among bone marrow cells of Epo-treated regressors as well as marked splenomegaly that might also reflect increase in progenitor cells. We assume that Epo in vivo is not restricted to the erythroid lineage but induces a broad spectrum of primitive hematopoietic progenitor cells (mostly primitive $Lin^-$, $Sca^+$, $kit^+$ and more committed $Lin^-$, $Sca^-$ bone marrow progenitor cells). Thus, Epo can be considered as an anti-cancer immune therapeutic agent through the generation of specific anti-tumor immune responses, besides its anti-anemia activity.

The animal data as well as the confirmation of the preliminary clinical observation suggest that rHuEpo may improve the biological and clinical course of at least some cancer patients.

REFERENCES

1. Bergsagel DE: Plasma cell myeloma. In: Hematology, Fourth edition, Eds: W. J. Williams et al.; McGraw-Hill, N.Y., pp. 1114–1141, 1990.
2. Cazzola M et al. Blood 86: 4446–53, 1995.
3. Durie B G M & Salmon S E. Cancer 36: 842–52, 1975.
4. Eschbach J W et al. N Engl J Med 321: 158–63, 1989.
5. Haran-Ghera, N. et al. J. Immunol. 126: 1241–1244, 1981.
6. Henry D H et al. Ann Intern Med 117: 739–48, 1992.
7. Kyle R A. Mayo Clin Proc 50: 29–37, 1975.
8. Lin F K et al. Proc Natl Acad Sci USA 82: 7580, 1985.
9. Ludwig H et al. 322: 1693–9, 1990.
10. Ludwig H et al. Ann Oncol 4: 161–7, 1993 a.
11. Ludwig et al. Europ J Cancer 29A (Suppl 2): s8–12, 1993 b.
12. Miller C B et al. N Engl J Med 322: 1689 –92, 1990.
13. Mittelman M et al. Blood 80: 841, 1992.
14. Mittelman M. Acta Haematol 90:53–7, 1993.
15. Mittelman M et al. Acta Haematol 98: 204–10, 1997.
16. Morere J F et al. Prog Urol 7:399–402, 1997.
17. Neumann, D. et al. J. Biol. Chem. 268: 13639–13649, 1993.
18. Potter, M. and Walters, J. L. J. Natl. Cancer Inst. 51: 875–880, 1973.
19. Rubbins J. Ann Intern Med 122: 676–7, 1995.
20. Schreiber S et al. N Engl J Med 334:619–23, 1996.
21. Spivak J L. Blood 84: 997–1004, 1994.
22. Spivak J L et al. Blood 77: 1228–33, 1991.

What is claimed is:

1. A method for treatment of a multiple myeloma patient, comprising administering to said patient an amount of erythropoietin effective, and in a protocol effective, for inhibition of tumor growth, wherein said amount and protocol are such that the administration continues for a sufficient time to result in said inhibition of tumor growth in said patient.

2. The method according to claim 1 wherein the erythropoietin is recombinant human erythropoietin.

3. A method for treatment of a multiple myeloma patient, comprising administering to said patient an amount of erythropoietin effective, and in a protocol effective, for triggering of tumor regression, wherein said amount and protocol are such that the administration continues for a sufficient time to result in said triggering of tumor regression in said patient.

4. The method according to claim 3 wherein the erythropoietin is recombinant human erythropoietin.

5. A method for treatment of a multiple myeloma patient, comprising administering to said patient an amount of erythropoietin effective, and in a protocol effective, for inhibition of multiple myeloma cell metastasis in said patient, wherein said amount and protocol are such that the administration continues for a sufficient time to result in said inhibition of multiple myeloma cell metastasis in said patient.

6. The method according to claim 5 wherein the erythropoietin is recombinant human erythropoietin.

* * * * *